United States Patent [19]

Lemieux

[11] Patent Number: 4,952,207
[45] Date of Patent: Aug. 28, 1990

[54] I.V. CATHETER WITH SELF-LOCATING NEEDLE GUARD

[75] Inventor: Francis P. Lemieux, Palm Harbor, Fla.

[73] Assignee: Critikon, Inc., Tampa, Fla.

[21] Appl. No.: 217,246

[22] Filed: Jul. 11, 1988

[51] Int. Cl.⁵ ............................................. A61M 5/18
[52] U.S. Cl. ............................ 604/164; 604/168; 604/198
[58] Field of Search ............................ 604/164–169, 604/158, 162, 263, 192, 198, 110

[56] References Cited

U.S. PATENT DOCUMENTS

| 3,536,073 | 10/1970 | Farb . | |
|---|---|---|---|
| 3,612,050 | 4/1969 | Sheridan | 604/166 |
| 4,160,450 | 7/1979 | Doherty . | |
| 4,373,526 | 2/1983 | Kling | 604/198 |
| 4,500,312 | 2/1985 | McFarlane . | |
| 4,631,057 | 12/1986 | Mitchell . | |
| 4,676,783 | 6/1987 | Jagger et al. . | |
| 4,702,738 | 10/1987 | Spencer . | |
| 4,747,831 | 5/1988 | Kulli | 604/110 |
| 4,762,516 | 8/1988 | Luther et al. | 604/164 |
| 4,781,692 | 11/1988 | Jagger et al. | 604/164 |
| 4,804,371 | 2/1989 | Vaillancourt | 604/198 |
| 4,810,248 | 3/1989 | Masters et al. | 604/198 |
| 4,816,024 | 3/1989 | Sitar et al. | 604/263 |
| 4,819,659 | 4/1989 | Sitar | 604/198 |

Primary Examiner—John D. Yasko
Assistant Examiner—Denise W. DeFranco
Attorney, Agent, or Firm—W. Brinton Yorks, Jr.; Paul A. Coletti

[57] ABSTRACT

An I.V. catheter is described, including a catheter and hub assembly and a needle and hub assembly. A needle guard, including a tubular distal portion and a split proximal flange, is located about the needle at the distal end of the needle hub. The needle includes a slot near the needle tip. As the needle assembly is withdrawn from the catheter, the needle guard slides along the needle until the split flange engages the needle slot, which locks the tubular distal portion of the guard over the needle tip.

11 Claims, 3 Drawing Sheets

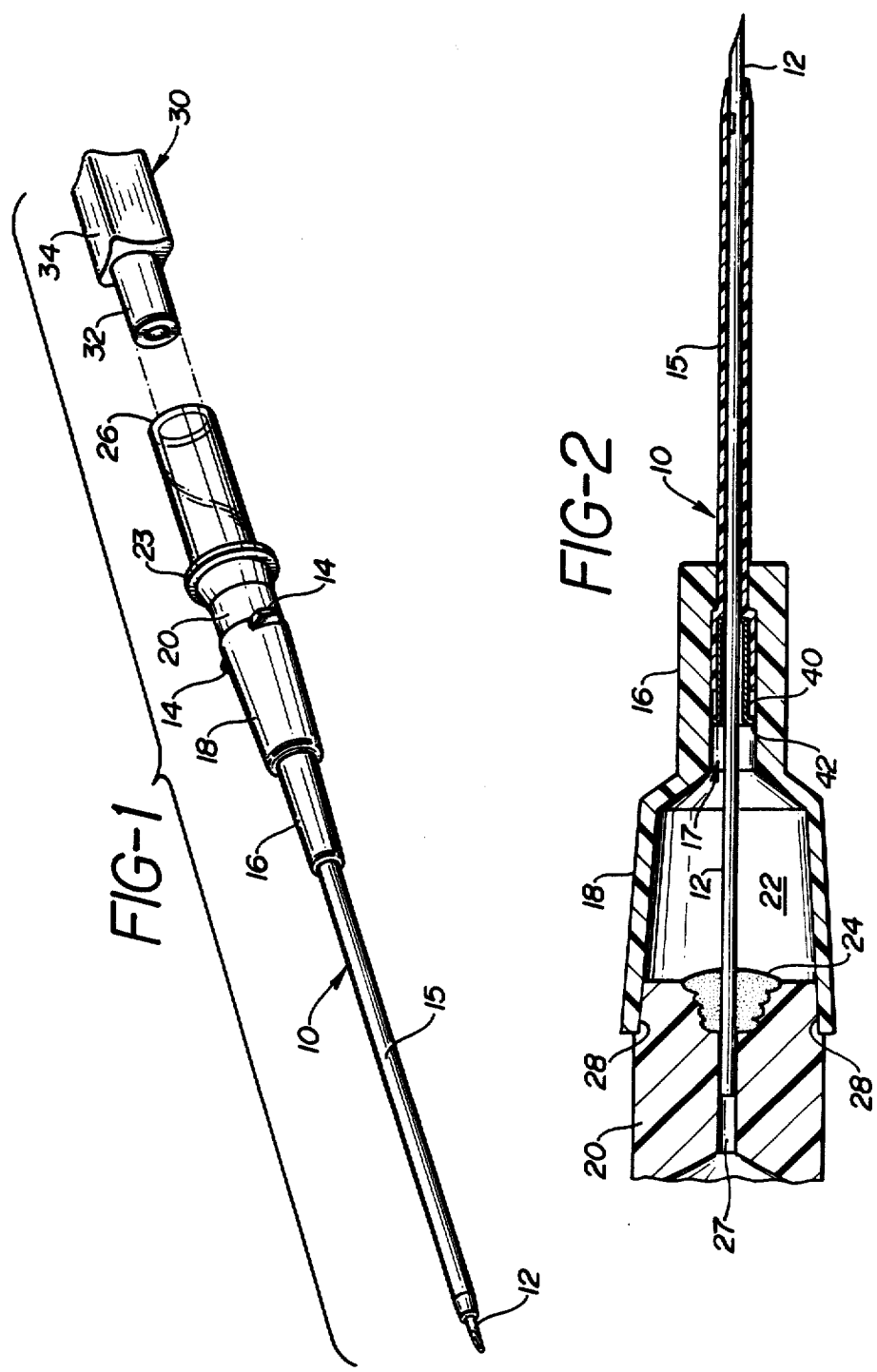

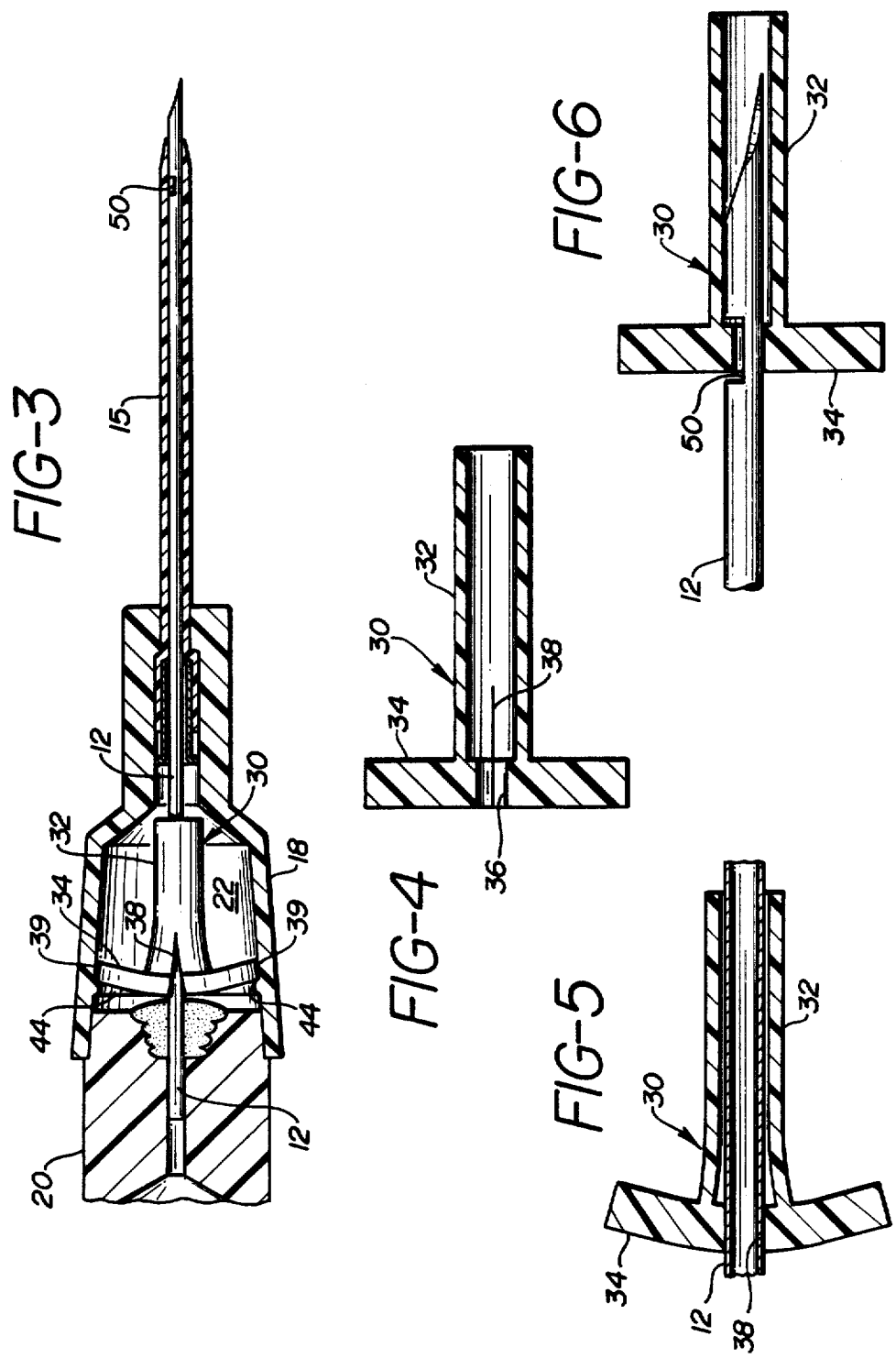

I.V. CATHETER WITH SELF-LOCATING NEEDLE GUARD

This invention relates to intravenous (I.V.) catheters and, in particular, to I.V. catheters which cover the cannula tip after use to prevent accidental injury from used needles.

Intravenous catheters for the infusion of fluids into the peripheral veins of a patient are one of the most common devices used in I.V. therapy. I.V. catheters may be produced in two general forms: through-the-needle catheters, in which a catheter is threaded through the needle cannula and into the vein of a patient, and over-the-needle catheters, in which the needle and concentric outer catheter are inserted into the vein and the needle is withdrawn through the emplaced catheter.

A typical over-the-needle I.V. catheter requires the user to remove and then dispose of a contaminated needle after the needle tip and catheter are properly located in the vein of the patient. Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon. For reasons of the desirability of protecting the user from exposure to hepatitis and AIDS, there is an increasing need to protect the user from accidental needle injury.

A catheter design which is directed toward this need is shown in U.S. patent application Ser. No. 022,132, filed Mar. 5, 1987, now U.S. Pat. No. 4,762,516. The catheter shown in this application includes an elongate body which houses a sliding needle guard. As the needle is withdrawn from the emplaced catheter, the user pushes the tab at the distal end of the needle guard, thereby sliding the needle guard out of the housing and along the needle, until the distal end of the guard covers the needle tip and the proximal end of the guard locks in the housing. The needle and guard may then be set aside with the needle tip fully protected.

While the arrangement described in this patent application provides full protection against accidental needle injury, the requirement of a sliding needle guard which exceeds the length of the needle necessarily requires a rather long and bulky assembly. Moreover, since the user must push the guard tab along the full length of the needle before the guard will lock in place over the needle tip, the arrangement is somewhat cumbersome to operate for users with small hands and fingers.

Accordingly it would be desirable for a needle to be securely protected by a small needle guard, and it would be most preferable for the needle guard to be moved into position over the needle tip automatically upon withdrawal of the needle from the patient, without the intervention of any special motion by the user.

In accordance with the principles of the present invention, an I.V. catheter with a self-locating needle guard is provided. The needle guard is located about the needle at the jointure of the needle and needle hub. Prior to use of the catheter the guard, which is of sufficient length to cover just a distal portion of the needle, is located within the catheter hub. At its proximal end the tubular guard includes a split locking flange, which retains the guard within the interior of the catheter hub. The guard will remain within the catheter hub while the needle is withdrawn from the patient until the locking flange engages a slot located near the distal end of the needle. The guard will then lock in place over the needle tip as the needle is fully withdrawn from the catheter.

In the drawings:

FIG. 1 illustrates an I.V. catheter in perspective and constructed in accordance with the principles of the present invention;

FIG. 2 illustrates the I.V. catheter of FIG. 1 in partial cross-section without a needle guard;

FIG. 3 illustrates the cross-sectional view of FIG. 2 with the needle guard in place in the catheter hub;

FIG. 4 illustrates the needle guard of FIG. 3 in cross-sectional detail

FIG. 5 illustrates the needle guard when positioned at the proximal end of the needle; and FIG. 6 illustrates the needle guard when locked at the distal end of the needle;

Figure 7:
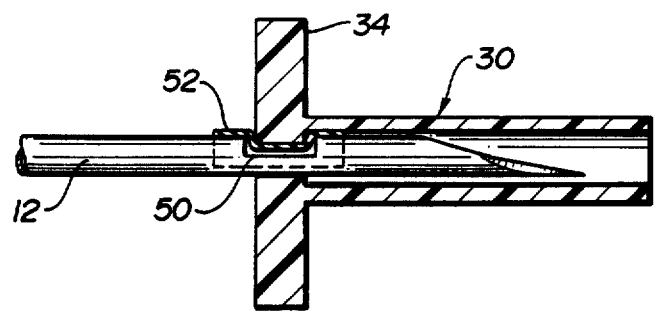
FIG. 7 illustrates in partial cross-section an alternate embodiment of the slotted I.V. catheter needle of the present invention.

Referring first to FIG. 1, an I.V. catheter constructed in accordance with the principles of the present invention is shown. The catheter 10 comprises a tube 15 made of fluorinated ethylene propylene or polyurethane material. The tube 15 is tapered at its distal end where it may easily slide into an opening in the patient's body formed by a hollow needle 12. The proximal end of catheter tube 15 is concentrically affixed within the distal end of a catheter hub 16, 18. The dual diameter hub terminates at its proximal end in a tab or fitting 14, suitable for attaching the catheter hub to a tubing set which administers a source of intravenous fluid.

The catheter 10 is engaged by the hollow needle 12, which is affixed at its proximal end to a needle hub 20. The needle hub 20 is hollow and includes a proximally located flange 23. Molded to the flange is a hollow flash chamber 26, which is made of a transparent or translucent polymer such as polypropylene or polycarbonate. The proximal end of the needle terminates in the hub 20, just short of the flash chamber.

Inserted into the flash chamber 26 (but shown separated just prior to insertion in FIG. 1) is a flash plug 30. The flash plug 30 is made of a polymeric material and will frictionally remain in place when inserted into the flash chamber. The flash plug body comprises a smaller diameter distal end 32 sized for a frictional fit in the flash chamber 26, and a somewhat square proximal end 34 with convex sides, which enables the flash plug to be easily grasped and inserted into the flash chamber. The flash plug 30 is hollow with an aperture 36 extending completely through the flash plug body. The distal opening of the aperture 3 is visible in FIG. 1. An insert made of a porous material is located within the aperture 36. The porous insert is pervious to the flow of air out of the flash chamber as the chamber fills with blood, but the pores of the insert are small enough to impede any blood flow therethrough.

Referring next to FIG. 2, the catheter 15 and its hub 16, 18, and the needle 12 and needle hub 20 are shown in cross-sectional detail. The proximal end of the catheter 15 is secured within passageway 17 of the distal end 16 of the catheter hub by a sleeve 40. The sleeve 40 is positioned within the proximal end of the lumen of the catheter 15. By forcing sleeve 40 into the lumen of the catheter, the sleeve effects an expansion of the proximal end of the catheter into contact with the internal surface of the passageway 17, thereby locking the hub and catheter together to prevent axial movement therebetween. The sleeve 40 is outwardly tapered at its proximal end to form a flange 42 which acts to securely position the sleeve 40 relative to the passageway 17.

The hollow needle 12 extends from its distal tip through the catheter 15 and sleeve 40, and into a passageway 27 in the center of the needle hub 20. The proximal portion of the needle 12 is affixed by epoxy 24 at the distal end of the needle hub 20. The proximal end of the needle 12 extends beyond the epoxy and into the passageway so that the lumen of the needle will not become filled with epoxy during the attachment procedure.

The distal end 28 of the needle hub 20 is of a lesser diameter than the major portion of the needle hub. This lesser diameter end is dimensioned to engage the open proximal end of the catheter hub 18.

In a conventional catheter and introducer needle assembly, the lesser diameter distal end of the needle hub is generally elongated and tapered to substantially occupy the proximal interior of the catheter hub. In the catheter assembly of the present invention, it may be seen that the major portion 22 of the cavity within the proximal end 18 of the catheter hub is unoccupied, with only the needle 12 extending through this region. The reason for reserving this space within the catheter hub is made clear with reference to FIG. 3.

In FIG. 3 it may be seen that a needle point guard 30 is located within the cavity of the catheter hub. FIG. 4 is an enlarged cross-sectional view of the needle Point guard 30, which resembles a flanged cylinder. The cylindrical distal portion 32 of the guard has an internal aperture with a diameter that enables the portion 32 to slide smoothly along the needle 12. The inner diameter of the cylindrical portion 32 is thus just slightly larger than the outer diameter of the needle. At the proximal end of the guard 30 is a circular locking flange 34 with a central aperture 36 that is concentric with that of the cylindrical portion 32. The diameter of the flange aperture 36 is slightly less than the outer diameter of the needle 12. The flange 34 and a proximal portion of the cylindrical portion 32 is slit horizontally by an expansion slot 38. The needle point guard 30 is made of a flexible material so that the flange and cylindrical portion will flex open and closed again as described below.

Referring concurrently to FIGS. 3 and 5, when the catheter and introducer needle are assembled prior to use, the needle point guard is slipped over the point of the needle to slide to a position adjacent the distal end of the needle hub 20. Since the flange aperture 36 is slightly smaller than the outside diameter of the needle, the needle will spread the needle point guard open at the expansion slot 38. The catheter and catheter hub are slipped over the needle until the hub 18 engages the distal end of the needle hub as shown in FIG. 3. The needle point guard 30 is thereby enclosed within the cavity 22 of the catheter hub. The spreading of the flange 34 causes the top and bottom of the flange to engage the inner wall of the catheter hub, as indicated at 39. The needle point guard is thus snugly retained within the catheter hub cavity 22. To ensure retention of the needle point guard within the cavity 22, it may further be desirable to form projections extending from the inner wall of the catheter hub just proximal the intended location of the guard, as indicated at 44.

After the user has properly positioned the needle tip and distal end of the catheter within the artery or vein of a patient, as indicated by the presence of blood in the flash chamber, the needle and needle hub are withdrawn from the catheter in preparation for attachment of a tubing set to the catheter hub. As the needle is initially withdrawn, the needle point guard 30 slides along the needle, but remains in position in the cavity 22 due to the engagement of the flange 34 and catheter hub at 39. The needle point guard 30 slides along the needle as shown in FIG. 5. Finally, the needle is withdrawn so that an engagement slot 50 near the tip of the needle 12 becomes aligned with the flange 34. At this moment the expansion slot 38 of the guard springs closed as the rim of the flange about aperture 36 is captured in engagement with the slot 50. Since the flange is no longer spread it is no longer retained within the catheter hub, but will leave the cavity 22 in engagement with the needle 12 and slot 50, as shown in FIG. 6. The needle may then be safely set aside without danger of accidental injury.

In an I.V. catheter constructed in accordance with the principles of the present invention, it may be desirable to insure that the initial "flash" of blood resulting from successful venipuncture be directed immediately through the needle lumen to the flash chamber 26, without any blood leakage out the engagement slot 50. To provide for this performance, the engagement slot 50 may be covered by a thin membrane 52 as shown in FIG. 7. The membrane may partially or completely surround the needle 12 at the slot location. The membrane will seal the engagement slot to prevent blood leakage out of the needle at this point, but must be sufficiently flexible so that it will distend without rupturing as the guard flange 34 engages the slot 50. The needle point guard 30 will thus be securely engaged in the engagement slot 50 while the membrane 52 prevents any blood leakage through the slot.

However, for some applications it may be desirable to take advantage of the open engagement slot 50. The standard technique for venipuncture requires the practitioner to visualize blood in the needle hub flash chamber to ascertain that the needle tip and catheter are within the vessel. For small sizes of I.V. catheters the flash of blood is very small, and is inhibited from immediate visualization by the length of travel to the flash chamber. Moreover, there is the further distraction of having to avert one's vision between the venipuncture site and the flash chamber at the proximal end of the catheter. Accordingly it would be desirable to provide for more rapid detection of the blood flash, and to obviate the need for the practitioner to avert his vision from the venipuncture site.

Figure 8:
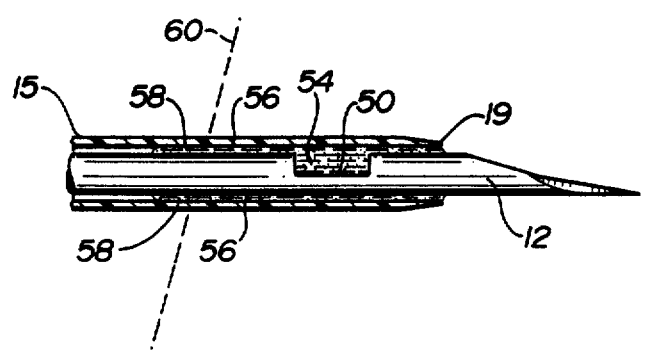
FIG. 8 illustrates in partial cross-section a slotted I.V. catheter needle arranged for prompt blood flash detection.

These objectives may be met by utilizing the slot 50 for early detection of even a small flash of blood. As shown in FIG. 8, the slot 50 is located just proximal the needle tip and the tapered distal end 19 of the catheter 15. When the blood vessel is punctured the blood will flow up the lumen of the needle to the slot 50, where it will fill the slot cavity as shown at 54. The blood will then flow through the small space between the needle 12 and the catheter 15 as shown at 56. When this interlumenal blood flow extends beyond the skin line (indicated schematically by dashed line 60), the blood will be visible between the catheter and needle as shown at 58. This small flash of blood 58 will thus be readily visible through the transparent or translucent catheter at the venipuncture site, indicating to the practitioner that the venipuncture was successful.

It may be appreciated that the detection of blood flash in this manner obviates the need for the flash chamber at the proximal end of the needle hub. Consequently, blood leakage from a vented flash plug may be prevented. Furthermore, it is also not necessary for blood to fill the entire needle lumen which may if desired be blocked or terminated proximal the slot 50. Rapid detection of even a small blood flash is accordingly enhanced.

From the foregoing description of the present invention, additional enhancements and modifications will be apparent to the user. For instance, to insure proper alignment between the engagement slot 50 and the flange 34 of the needle point guard, it may be desirable to form mating slots and projections in the inside of the catheter hub 18 and the outer periphery of the distal end 28 of the needle hub 20 and the edges 39 of the needle point guard. By tracking the catheter components in this manner the longitudinal edges of the engagement slot 50 will be maintained in alignment with the expansion slot 38 of the guard for assured engagement of the guard flange in the engagement slot.

What is claimed is:

1. An I.V. catheter with a self-locating needle guard comprising:
   a catheter assembly including a catheter attached to a hollow catheter hub;
   an introducer needle assembly, including a hollow needle with a distal tip, said needle being affixed near its proximal end to a needle hub, the distal end of said needle hub being suitable for engagement with said hollow catheter hub, and said needle including means for engaging a needle guard; and
   a needle guard including a proximal portion having means for engaging said engaging means of said needle and a distal portion for extending over said needle tip when said proximal portion is engaged with said engaging means of said needle, said needle guard located proximal said catheter and distal said needle hub and mounted for relative motion with respect to said needle as said needle is withdrawn from said catheter until said engaging means of said needle guard engages said engaging means of said needle; and
   retaining means for retaining said needle guard within said catheter hub prior to engagement of said needle engaging means and said needle guard engaging means.

2. The I.V. catheter of claim 1, wherein said engaging means of said needle comprises an engagement slot located near said distal tip of said needle.

3. The I.V. catheter of claim 2, wherein said distal portion of said needle guard comprises a cylindrical portion having an inner diameter slightly larger than the outer diameter of said needle.

4. The I.V. catheter of claim 3, wherein said proximal portion of said needle guard comprises a flange having a central aperture aligned with said distal cylindrical portion, and said needle guard engaging means includes an axially aligned expansion slot passing through said flange.

5. The I.V. catheter of claim 4, wherein said needle guard becomes locked in engagement with said needle when the rim of said flange aperture engages said engagement slot of said needle.

6. The I.V. catheter of claim 4, wherein the diameter of said flange aperture is less than the outer diameter of said needle,
   whereby said needle spreads said flange about said expansion slot when the full diameter of said needle passes through said flange aperture.

7. The I.V. catheter of claim 1, wherein said proximal portion of said needle guard comprises a radially extending flange having a central aperture, and said retaining means includes an axially aligned expansion slot passing through said flange,
   whereby said flange is brought into contact with said catheter hub when said expansion slot opens in response to the passage of said needle through said central aperture.

8. An I.V. catheter with a self-locating needle guard comprising:
   a catheter assembly including a catheter attached to a catheter hub;
   an introducer needle assembly for connection with said catheter assembly, including a hollow needle with a distal tip and a needle hub, said needle being affixed near its proximal end to extend distally exposed from the distal end of said needle hub, and said needle including means located distal said distal end of said needle hub for engaging a needle guard; and
   a needle guard, initially located about said needle at the distal end of said needle hub and capable of axial movement relative to said needle, said needle guard including a proximal portion having means for engaging said engaging means of said needle and a distal portion for extending over said needle tip when said proximal portion is engaged with said engaging means of said needle; and
   retaining means for retaining said needle guard within said catheter hub prior to engagement of said needle engaging means and said needle guard engaging means.

9. The I.V. catheter of claim 1, wherein said catheter hub further includes means for retaining said needle guard within said catheter hub prior to engagement of said needle engaging means and said needle guard engaging means.

10. The I.V. catheter of claim 9, wherein said retaining means includes a projection extending from said catheter hub and abutting said needle guard prior to engagement of said needle engaging means and said needle guard engaging means.

11. The I.V. catheter of claim 3, wherein said proximal portion of said needle guard includes an expandable central aperture which, in its unexpanded condition, has an inner diameter which is less than the outer diameter of said needle.

* * * * *